(12) United States Patent
Schaeffer et al.

(10) Patent No.: US 8,007,490 B2
(45) Date of Patent: Aug. 30, 2011

(54) REDUCED WIDTH DUAL-LUMEN CATHETER

(75) Inventors: Darin G. Schaeffer, Bloomington, IN (US); Eric R. Hennessy, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 11/875,505

(22) Filed: Oct. 19, 2007

(65) Prior Publication Data

US 2009/0105690 A1    Apr. 23, 2009

(51) Int. Cl.
*A61M 25/00* (2006.01)
(52) U.S. Cl. ........................................ 604/528; 604/523
(58) Field of Classification Search .................. 604/524, 604/526, 284, 27, 527, 43, 528, 525, 523, 604/93.01
See application file for complete search history.

(56) References Cited

U.S. PATENT DOCUMENTS

| | | | |
|---|---|---|---|
| 5,743,875 A | 4/1998 | Sirhan et al. | |
| 5,868,706 A | 2/1999 | Cox | |
| 6,013,069 A | 1/2000 | Sirhan et al. | |
| 6,027,475 A * | 2/2000 | Sirhan et al. | 604/96.01 |
| 6,544,218 B1 * | 4/2003 | Choi | 604/96.01 |
| 6,786,884 B1 * | 9/2004 | DeCant et al. | 604/43 |
| 7,011,647 B2 * | 3/2006 | Purdy et al. | 604/164.04 |
| 2001/0012927 A1 * | 8/2001 | Mauch | 604/284 |
| 2006/0206111 A1 * | 9/2006 | Young | 606/44 |

* cited by examiner

*Primary Examiner* — Kevin C Sirmons
*Assistant Examiner* — Brandy C Scott
(74) *Attorney, Agent, or Firm* — Brinks Hofer Gilson & Lione

(57) ABSTRACT

A dual-lumen catheter for use in a body vessel. The catheter includes an elongate shaft having a longitudinal axis and defining at least a first and a second lumen. The elongate shaft has a cross sectional width normal to the longitudinal axis and a webbing section disposed between the two lumens. The webbing section has a webbing length less than the cross sectional width to reduce a tendency of the shaft to bend perpendicular to the webbing length when the shaft is rotated.

15 Claims, 3 Drawing Sheets

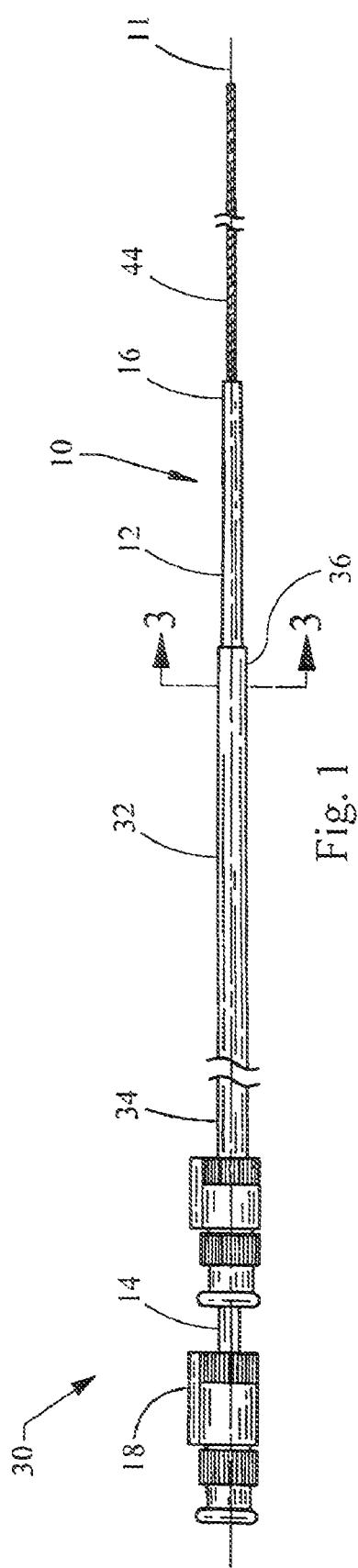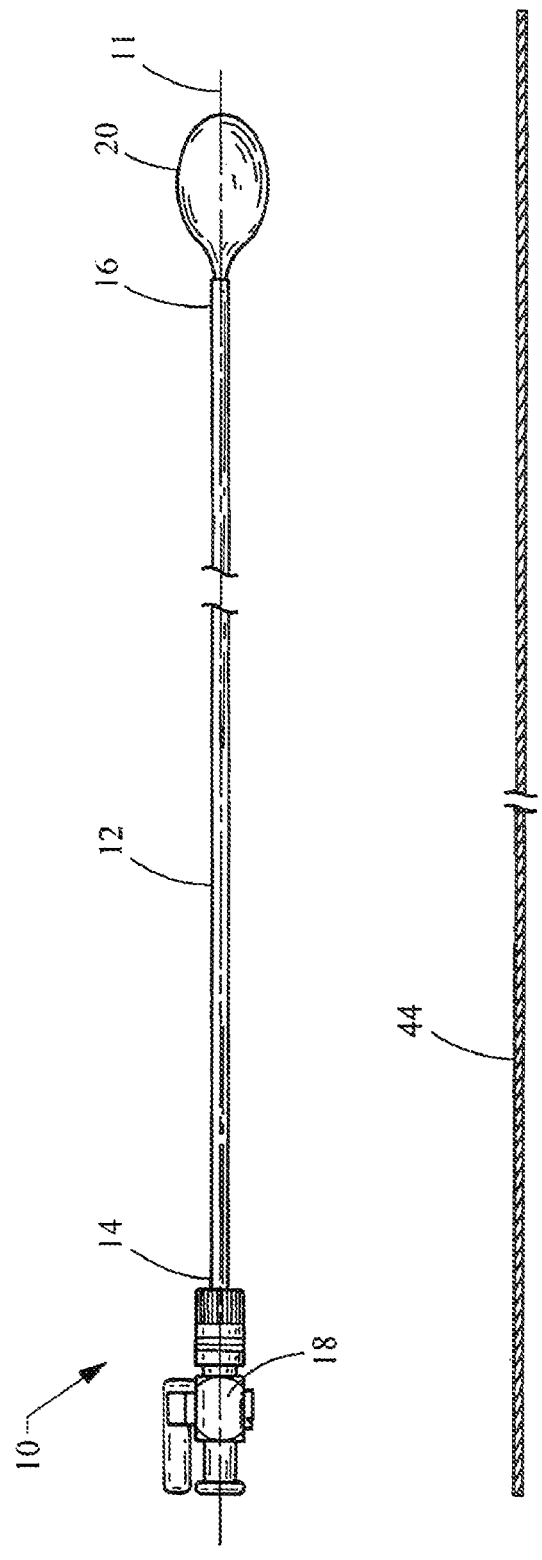

REDUCED WIDTH DUAL-LUMEN CATHETER

BACKGROUND OF THE INVENTION

1. Field of the Invention

The present invention generally relates to medical catheters. More specifically, the invention relates to dual-lumen catheters.

2. Description of Related Art

Dual-lumen catheters are often used for the treatment of conditions relating to body vessels such as arteries and veins. When treating, for example, a stenosis or other lesion a wire guide may be percutaneously inserted into the body vessel and positioned near the lesion. One lumen of the catheter is inserted over a wire guide and a distal tip of the catheter is guided to a treatment location by pushing the catheter along the wire guide. Once at the treatment location a balloon, for example, may be unfolded and inflated through the other lumen to temporally occlude the vessel. In some cases, a stent may be disposed around the balloon in which case inflation of the balloon positions and expands the stent within the body vessel. In other cases, the wire guide may be removed and another treatment device provided through the wire guide lumen to treat the lesion.

Often it is necessary to rotate the dual-lumen catheter around its longitudinal axis when advancing it to the treatment location or otherwise positioning it in the vasculature. With existing dual-lumen catheters having a round shaft, this results in a "whipping" effect when the catheter is rotated that may cause injury to the vasculature. The "whipping" effect occurs because of a tendency of round catheters to bend normal to a webbing axis located between the two lumens.

In view of the above, it is apparent that there exists a need for an improved dual-lumen catheter.

SUMMARY OF THE INVENTION

In satisfying the above need, as well as overcoming the enumerated drawbacks and other limitations of the related art, the present invention provides a dual-lumen catheter including an elongate shaft having a longitudinal axis and defining at least a first and a second lumen. The elongate shaft has a cross sectional width normal to the longitudinal axis. A webbing section located between the two lumens and has a webbing length less than the cross sectional width. Preferably, the webbing section is perpendicular to the cross sectional width. Alternately, it is possible for the webbing section to be at an acute angle to the cross sectional width.

In one embodiment, a perimeter of a cross section normal to the longitudinal axis defines an out of round shape including, for example, an ellipse or an egg shape. In another embodiment, the perimeter of the cross section normal to the longitudinal axis defines a polygon. In one example, the polygon includes a plurality of flat sides. In a second example, the polygon includes ten sides.

Depending on the needs of a particular application, the catheter may be made of at least one of nylon, polyester, polytetrafluroethylene, latex, rubber, and mixtures thereof.

The present invention also includes a catheterization assembly for use in a body vessel including an introducer sheath having a sheath wall defining a sheath inner diameter and a sheath lumen extending therethrough. Any of the dual-lumen catheter's described herein may be received by the sheath lumen for relative axial and rotational movement therein. In addition, a wire guide may be disposed within one of the lumens for relative axial movement therein to guide the catheter to a treatment location in the body vessel.

The present invention further includes a method of treating a body vessel including providing any of the dual-lumen catheters described herein into a body cavity. The method also includes translating a distal end of the catheter adjacent a desired treatment location, deploying a treatment means for treating the body cavity, and withdrawing the catheter from the body vessel.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 1 is a side view of one embodiment of a catheterization assembly for use with a dual-lumen catheter according to the present invention;

FIG. 2 is an exploded view of the catheterization assembly of FIG. 1;

DETAILED DESCRIPTION

Figure 3:
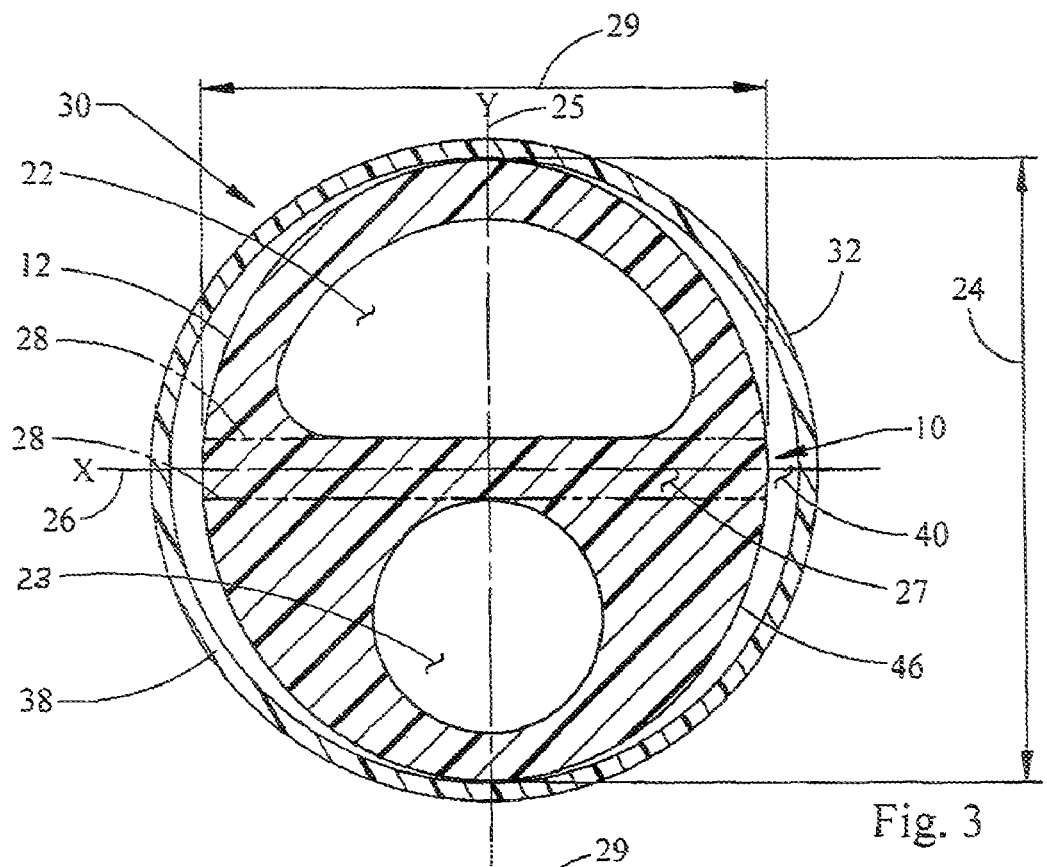
FIG. 3 is a section view along line 3-3 of FIG. 1 showing one embodiment of the present invention.

Referring now to FIGS. 1 and 2, a dual-lumen catheter embodying the principles of the present invention is illustrated therein and designated at 10. The dual-lumen catheter 10 is a primary component of a catheterization assembly 30 for treatment of a body vessel (not shown). The catheterization assembly 30 also includes an introducer sheath 32 receiving the dual-lumen catheter 10 along with a wire guide 44 disposed within one of the catheter lumens.

The dual-lumen catheter 10 includes an elongate shaft 12 extending along a longitudinal axis 11 from a proximal end 14 to a distal end 16. The proximal end 14 preferably includes a hub 18 to provide access to the lumens of the catheter 10. In this particular embodiment, the distal end 18 includes an inflatable balloon 20. However, any other treatment device appropriate for a dual-lumen catheter may also be provided without falling beyond the scope of the present invention. The introducer sheath 32 and catheter 10 are made of any appropriate flexible material for use in a body vessel. The material may include, for example, nylon, polyester, polytetrafluroethylene (PTFE), latex, rubber and mixtures thereof.

Turning to FIG. 3, a sectional view through the catheterization assembly 30 taken normal to the longitudinal axis 11 is shown (see FIG. 1). The sheath 32 includes a sheath wall 38 defining a sheath lumen 40 having a sheath inner diameter. As indicated above, the catheter 10 is received within the sheath lumen 40 for relative axial and rotational movement therein.

The elongate shaft 12 of the catheter 10 defines at least a first and a second lumen 22 and 23 formed therethrough and substantially parallel to the longitudinal axis 11. The first lumen 22 may, for example, be an inflation lumen in fluid communication with the balloon 20. The second lumen 23 may, for example, be a wire guide lumen for receiving the wire guide 44. The shaft 12 has a cross sectional width 24 along a cross sectional vertical axis 25 normal to the longitudinal axis 11. A webbing section 27 is disposed between the first and second lumens 22 and 23 and is demarcated by the phantom lines 28. In this example, the webbing section 27 is defined along a cross sectional horizontal axis 26 perpendicular to the cross sectional vertical axis 25. However, in other examples it is possible for the webbing section 27 to be oriented at an acute angle to the vertical axis 25 (not shown).

The webbing section 27 has a webbing length 29 less than the cross sectional width 24. As a result, a perimeter 46 of the cross section of the shaft 12 normal to the longitudinal axis 11 defines an out of round shape. In the example shown, the out of round shape includes an ellipse, while other examples include an egg shaped perimeter 46. Reducing the webbing length 29 relative to the cross sectional width 24 decreases the tendency of the catheter 10 to "whip" or bend perpendicular to the webbing length 29 when the shaft 12 is rotated.

Figure 4:
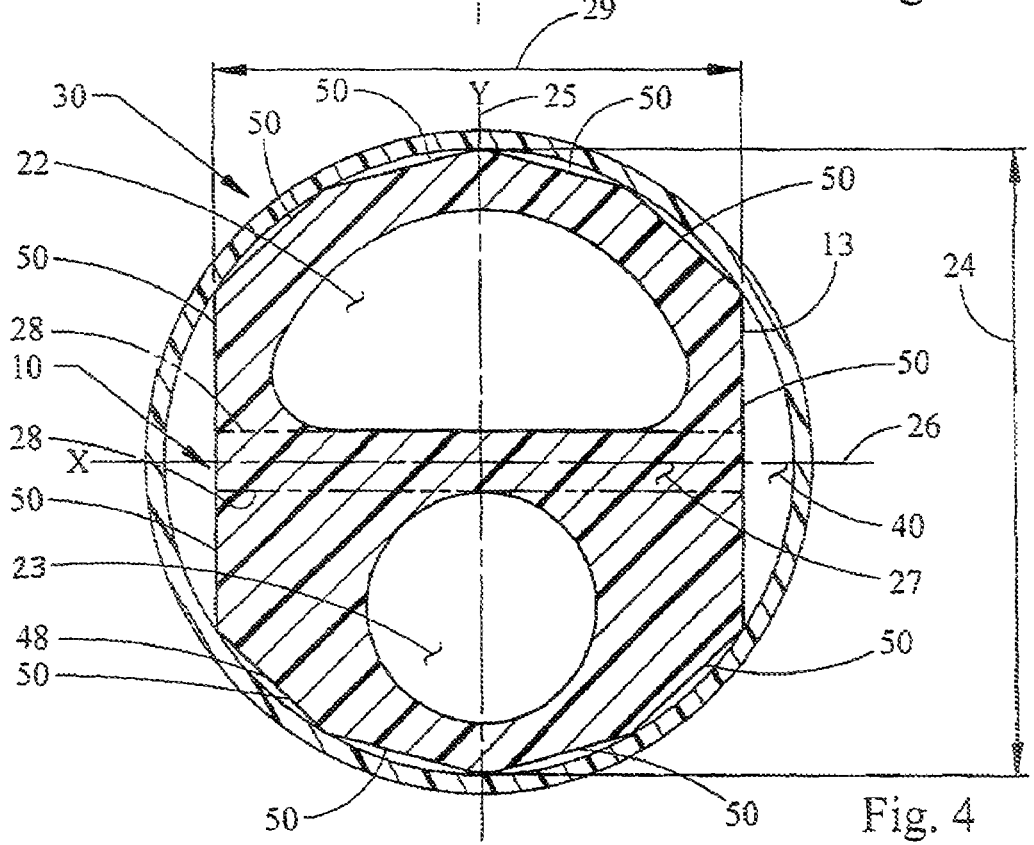
FIG. 4 is a section view along line 3-3 of FIG. 1 showing an alternate embodiment of the present invention.

FIG. 4 illustrates another embodiment of the present invention. In this embodiment, like features share like reference numbers with the embodiment of FIG. 3. As above, the webbing section 27 is defined between the first and second lumens 22 and 23 and is demarcated by the phantom lines 28 and has a webbing length 29 shorter than the cross sectional width 24. However, rather than an out of round shaft 12 this embodiment a multi-sided shaft 13. The shaft 13 may have any appropriate number of flat sides 50, although preferred examples include between two and ten sides. It should be appreciated that the present embodiment does not exclude the perimeter from having curved or arcuate sides combined with the flat sides 50.

Figure 5:
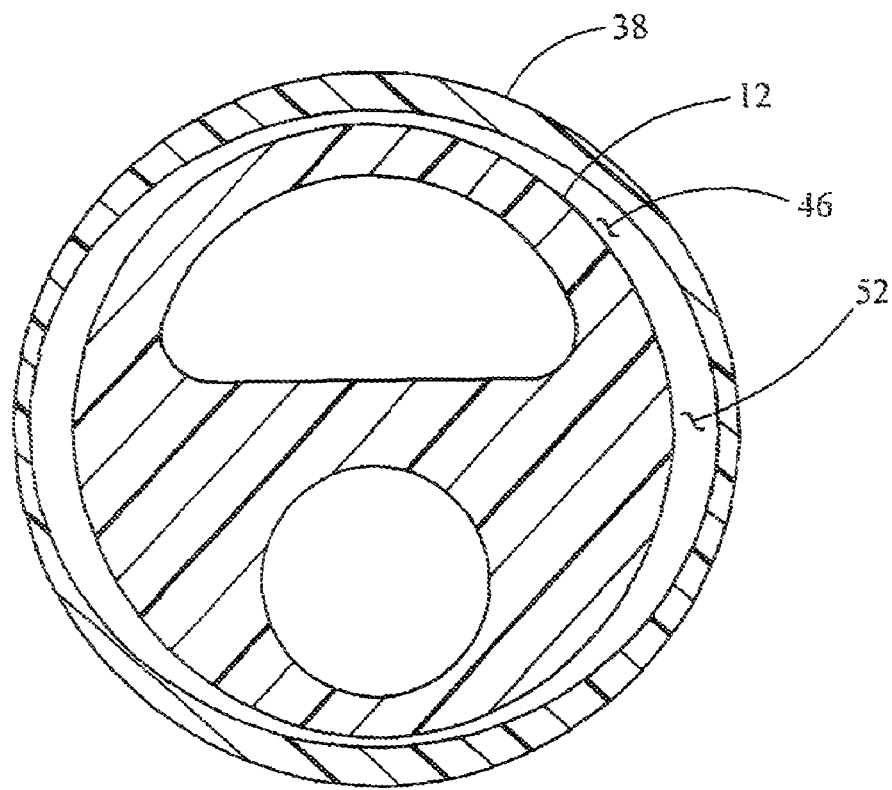
FIG. 5 is a section view along line 3-3 of FIG. 1 showing an area gained between an outer sheath of the catheterization assembly and the dual-lumen catheter.

Reducing the webbing length 29 also increases the space available within the sheath lumen 40 to, for example, inject contrast through the sheath lumen 40 and into the body vessel. FIG. 5 shows an area 50 gained between the sheath wall 38 and the shaft 12 compared to a round catheter shaft. As a result, more contrast, or another appropriate fluid, may be injected into the body vessel at a given pressure compared to the round shaft.

In the examples shown, the webbing length 29 is approximately 10% to 20% less than the cross-sectional width 24. In other examples, the length 29 may be 50% less than the width 24 or more. The exact proportions will vary for each application and will depend, for example, on the areas of the lumens 22 and 23.

Returning back to FIGS. 1 and 2, the catheterization assembly 30 for introducing the dual-lumen catheter 10 includes the introducer sheath 32 for percutaneously introducing the dual-lumen catheter 10 into the body vessel. The introducer sheath 32 is preferably made of polytetrafluoroethylene (PTFE), but any other suitable material may be used without falling beyond the scope or spirit of the present invention. The introducer sheath 32 extends from a proximal section 34 to a distal section 36 and may have any suitable size, for example, between about three-french to eight-french. The introducer sheath 32 serves to allow the dual-lumen catheter 10 to be percutaneously inserted to a desired location in the body vessel. The introducer sheath 32 receives the elongate shaft 12 of the catheter 10 and provides stability to the shaft 12 at a desired location of the body vessel. For example, the introducer sheath 32 is held stationary within a common visceral artery, and adds stability to the elongate shaft 12, as the shaft 12 is advanced through the introducer sheath 32 to a treatment area in the vasculature.

As shown, the assembly 30 may also include the wire guide 44 configured to be percutaneously inserted within the vasculature to guide the dual-lumen catheter 10 to the treatment area. The wire guide 44 provides the dual-lumen catheter 10 with a path to follow as it is advanced within the body vessel. The size of the wire guide 44 is based on an inside diameter of the wire guide lumen of the elongate shaft 12 and the diameter of the target body vessel.

When the distal end 16 of the shaft 12 is at the desired location in the body vessel, the wire guide 44 may be removed and a treatment means including, for example, a vascular filter device, a stent, fiber optics, or a balloon, may be coupled to a pushing member (not shown) and inserted into the wire guide lumen. It should be understood that the treatment means may include any medical treatment or device suitable for deployment through a catheter lumen. The pushing member is advanced through the wire guide lumen for deployment of the device or treatment through the distal end 16.

The elongate shaft 12 further has a proximal end 14 and a hub 18 configured to receive fluid in the inflation lumen for inflation of the balloon 20 and to receive the wire guide 44 and other treatment devices in the wire guide lumen for advancement therethrough. The size of the elongate shaft 12 is based on the size of the body vessel in which it percutaneously inserts, the size of the target vessel, and the size of any other devices to be deployed through the shaft 12 into the vasculature.

This embodiment may also retrieve devices by positioning the distal end 16 of the elongate shaft 12 adjacent the deployed device in the vasculature. A retrieval member is advanced through the wire guide lumen of the elongate shaft 12 until a distal part of the member protrudes from the distal end 16 of the shaft 12. The distal part is coupled to a retrieval end of the device after which the member is retracted proximally, drawing the device into the wire guide lumen.

It is understood that the assembly described above is merely one example of an assembly that may be used in a body vessel. Of course, other apparatus, assemblies and systems may be used with any embodiment of the dual-lumen catheter without falling beyond the scope or spirit of the present invention.

Figure 6:
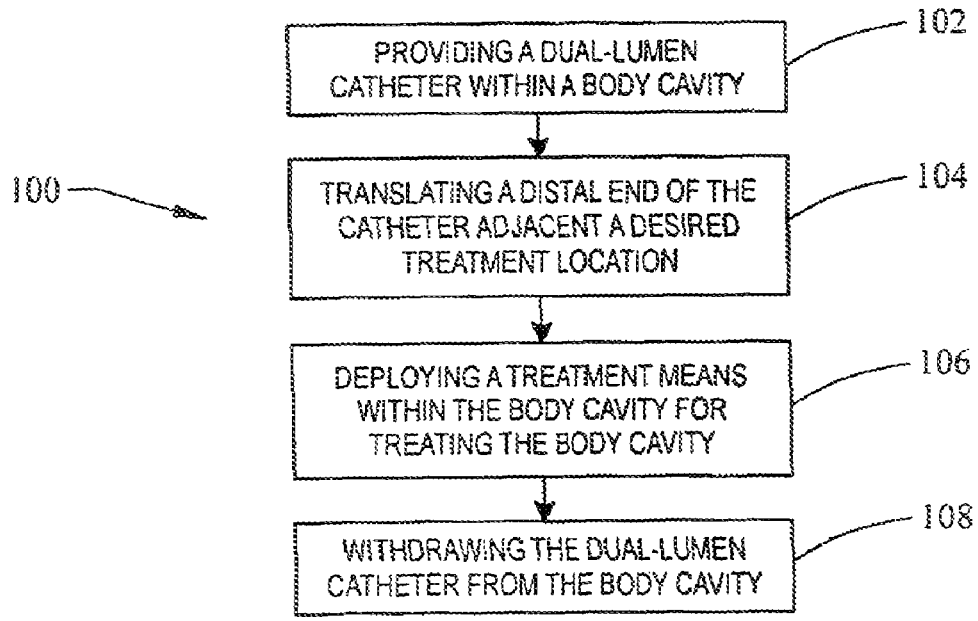
FIG. 6 is a flow chart describing a method of treating a body cavity with a dual-lumen catheter according to the present invention.

Turning to FIG. 6, it provides a flow chart designated at 100 describing a method for of filtering emboli from a body cavity including blood vessels. The method includes, at box 102, providing any of the dual-lumen catheters described herein within the body cavity. Box 104 includes translating a distal end of the catheter adjacent a desired treatment location. Box 106 includes deploying an appropriate treatment means within the body cavity for treating the body cavity, and box 108 includes withdrawing the dual-lumen catheter from the body cavity.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

We claim:

1. A dual-lumen catheter with a sheath having a wall for use in a body vessel, the catheter comprising:

an elongate shaft having a longitudinal axis and having at least a first lumen and a second lumen formed therethrough, the first and second lumens in non-coaxial relationship, the elongate shaft having a cross sectional width normal to the longitudinal axis and defining an area between the shaft and the sheath wall for fluid to be injected into the body vessel; and a webbing section being disposed between the at least first and second lumens, and wherein at least part of the webbing section has a substantially flat surface formed along at least one of the first and second lumens, the webbing section having a webbing length that is 10%-20% less than the cross sectional width, reducing the stiffness of the elongate shaft along the webbing length, wherein the webbing length is perpendicular to or at an acute angle to the cross sectional width, wherein an outer perimeter of a cross section of the elongate shaft normal to the longitudinal axis includes at least two flat sides that are positioned opposite of each other with the webbing length extending from a first side of the at least two flat sides of the outer perimeter to a second side of the at least two flat sides of the outer perimeter, the first and second lumens disposed between the two flat sides.

2. The catheter according to claim 1, wherein the webbing length is perpendicular to the cross sectional width.

3. The catheter according to claim 1, wherein the webbing length is at an acute angle to the cross sectional width.

4. The catheter according to claim 1, wherein the outer perimeter of the elongate shaft defines a polygon.

5. The catheter according to claim 4, wherein the polygon includes ten sides.

6. The catheter according to claim 1, wherein the elongate shaft is made of at least one of nylon, polyester, polytetrafluroethylene, latex, rubber, and mixtures thereof.

7. A catheterization assembly for use in a body vessel, the assembly comprising:
  an introducer sheath extending from a proximal section to a distal section with a sheath wall having a sheath inner diameter and defining a sheath lumen extending therethrough;
  a catheter shaft extending from a proximal end to a distal end along a longitudinal axis and being disposed within the sheath lumen for relative axial and rotational movement therein, the catheter shaft having at least an inflation lumen and a wire guide lumen formed therethrough and having a cross sectional width normal to the longitudinal axis and defining an area between the shaft and the sheath wall for fluid to be injected into the body vessel;
  a webbing section being disposed between at least the inflation and wire guide lumens, at least part of the webbing section having a substantially flat surface formed along at least one of the inflation and wire guide lumens, the webbing section having a webbing length that is at least 10% less than the cross sectional width to reduce the stiffness of the catheter shaft along the webbing length, wherein the webbing length is perpendicular to or at an acute angle to the cross sectional width, wherein an outer perimeter of a cross section of the elongate shaft normal to the longitudinal axis includes at least two flat sides that are positioned opposite of each other with the webbing length extending from a first flat side of the at least two flat sides of the outer perimeter to a second flat side of the at least two flat sides of the outer perimeter, the first and second lumens disposed between the two flat sides, the cross sectional width being smaller than the sheath inner diameter; and
  a wire guide being disposed within the wire guide lumen for relative axial movement therein for guiding the catheter shaft to a treatment location in the body vessel.

8. The catheterization assembly according to claim 7, wherein the webbing length is perpendicular to the cross sectional width.

9. The catheterization assembly according to claim 7, wherein the webbing length is at an acute angle to the cross sectional width.

10. The catheterization assembly according to claim 7, wherein the outer perimeter of the elongate shaft defines a polygon.

11. The catheterization assembly according to claim 7, wherein the introducer sheath and the elongate shaft are made of at least one of nylon, polyester, polytetrafluroethylene, latex, rubber, and mixtures thereof.

12. A method of treating a body cavity, the method comprising:
  providing a dual-lumen catheter in the body cavity, the catheter comprising an elongate shaft having a longitudinal axis and defining at least a first and a second lumen formed therethrough, the elongate shaft having a cross sectional width normal to the longitudinal axis and defining an area between the shaft and the sheath wall for fluid to be injected into the body vessel, and a webbing section disposed between at least the first and second lumens, at least part of the webbing section having a substantially flat surface formed along at least one of the inflation and wire guide lumens, the webbing section having a webbing length that is at least 10% less than the cross sectional width to reduce the stiffness of the elongated shaft along the webbing length, wherein the webbing length is perpendicular to or at an acute angle to the cross sectional width, wherein an outer perimeter of a cross section of the elongate shaft normal to the longitudinal axis includes at least two flat sides that are positioned opposite of each other with the webbing length extending from a first flat side of the at least two flat sides of the outer perimeter to a second flat side of the at least two flat sides of the outer perimeter, the first and second lumens disposed between the two flat sides;
  translating a distal end of the catheter adjacent a desired treatment location;
  deploying a treatment means for treating the body cavity; and
  withdrawing the catheter from the body vessel.

13. The catheter according to claim 1, wherein the stiffness of the elongate shaft along the webbing length is reduced such that the elongated shaft is without a tendency to bend normal to the webbing length for preventing a "whipping" effect during rotation of the elongated shaft about the longitudinal axis while positioned in the body vessel.

14. The catheterization assembly according to claim 7, wherein the stiffness of the catheter shaft along the webbing length is reduced such that the elongated shaft is without a tendency to bend normal to the webbing length for preventing a "whipping" effect during rotation of the catheter shaft about the longitudinal axis while positioned in the body vessel.

15. The method according to claim 12, wherein the stiffness of the elongate shaft along the webbing length is reduced such that the elongated shaft is without a tendency to bend normal to the webbing length for preventing a "whipping" effect during rotation of the elongated shaft about the longitudinal axis while positioned in the body vessel.

* * * * *